US010059913B2

(12) United States Patent
Ott

(10) Patent No.: US 10,059,913 B2
(45) Date of Patent: Aug. 28, 2018

(54) BIOARTIFICAL LUNG

(71) Applicant: The General Hospital Corporation, Boston, MA (US)

(72) Inventor: Harald C. Ott, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 343 days.

(21) Appl. No.: 14/685,158

(22) Filed: Apr. 13, 2015

(65) Prior Publication Data

US 2015/0291925 A1  Oct. 15, 2015

Related U.S. Application Data

(63) Continuation of application No. 13/375,260, filed as application No. PCT/US2010/037379 on Jun. 4, 2010, now Pat. No. 9,005,885.

(60) Provisional application No. 61/256,281, filed on Oct. 29, 2009, provisional application No. 61/184,170, filed on Jun. 4, 2009.

(51) Int. Cl.
*C12M 3/00* (2006.01)
*C12M 1/34* (2006.01)
*C12M 1/26* (2006.01)
*A61L 27/38* (2006.01)
*C12M 1/12* (2006.01)
*C12M 1/00* (2006.01)
*A61M 16/00* (2006.01)

(52) U.S. Cl.
CPC ......... *C12M 21/08* (2013.01); *A61L 27/3804* (2013.01); *A61L 27/3891* (2013.01); *C12M 25/14* (2013.01); *C12M 29/10* (2013.01); *C12M 33/00* (2013.01); *C12M 33/04* (2013.01); *C12M 41/30* (2013.01); *A61M 16/0054* (2013.01); *A61M 2210/1039* (2013.01)

(58) Field of Classification Search
CPC ............ A61L 27/3804; A61L 27/3891; A61M 16/0054; A61M 2210/1039; C12M 21/08; C12M 25/14; C12M 29/10; C12M 33/00; C12M 33/04; C12M 41/30
USPC ..................................... 435/284.1; 424/93.7
See application file for complete search history.

(56) References Cited

U.S. PATENT DOCUMENTS 4,446,229 A    5/1984 Indech
4,598,706 A *  7/1986 Darowski ............. A61M 16/00
                                                         128/205.23

(Continued)

FOREIGN PATENT DOCUMENTS

CA    2751133    2/2009
CN    1911438    2/2007

(Continued)

OTHER PUBLICATIONS

The Decision of Final Rejection of the Application in Chinese Application No. 201080032724.4, dated Jan. 27, 2015, 7 pages (English translation).

(Continued)

*Primary Examiner* — William H. Beisner
*Assistant Examiner* — Danielle B Henkel
(74) *Attorney, Agent, or Firm* — Fish & Richardson P.C.

(57) ABSTRACT

Presented is an airway organ bioreactor apparatus, and methods of use thereof, as well as bioartificial airway organs produced using the methods, and methods of treating subjects using the bioartificial airway organs.

12 Claims, 8 Drawing Sheets

(56) References Cited

U.S. PATENT DOCUMENTS

| | | | |
|---|---|---|---|
| 5,540,225 A * | 7/1996 | Schutt | A61K 9/0026 128/207.15 |
| 5,750,329 A | 5/1998 | Quinn et al. | |
| 6,087,552 A | 7/2000 | Kenton | |
| 6,416,995 B1 | 7/2002 | Wolfinbarger | |
| 6,479,064 B1 | 11/2002 | Atala | |
| 7,662,409 B2 | 2/2010 | Masters | |
| 9,005,885 B2 | 4/2015 | Ott | |
| 2002/0172705 A1 | 11/2002 | Murphy et al. | |
| 2002/0182241 A1 | 12/2002 | Borenstein et al. | |
| 2002/0182261 A1 | 12/2002 | Jainwu et al. | |
| 2003/0087428 A1 | 5/2003 | Wolfinbarger et al. | |
| 2003/0129751 A1 | 7/2003 | Grikscheit et al. | |
| 2003/0166274 A1 | 9/2003 | Hewitt et al. | |
| 2003/0180268 A1 | 9/2003 | Atala | |
| 2005/0107868 A1 | 5/2005 | Yasuhide et al. | |
| 2005/0196423 A1 | 9/2005 | Batich et al. | |
| 2005/0256588 A1 | 11/2005 | Sawa et al. | |
| 2007/0059293 A1 | 3/2007 | Atala | |
| 2007/0244568 A1 | 10/2007 | Matsuda et al. | |
| 2008/0017194 A1 * | 1/2008 | Hassanein | A01N 1/02 128/200.24 |
| 2008/0131473 A1 | 6/2008 | Brown et al. | |
| 2008/0292595 A1 | 11/2008 | Arbetman et al. | |
| 2008/0292677 A1 | 11/2008 | Cortiella et al. | |
| 2009/0035855 A1 | 2/2009 | Ying et al. | |
| 2009/0060961 A1 | 3/2009 | Naruse et al. | |
| 2009/0075282 A1 | 3/2009 | Mahmood et al. | |
| 2009/0142836 A1 | 6/2009 | Wang et al. | |
| 2009/0202977 A1 | 8/2009 | Ott et al. | |
| 2010/0034791 A1 | 2/2010 | Lelkes et al. | |
| 2010/0092433 A1 | 4/2010 | Levenberg et al. | |
| 2013/0084266 A1 | 4/2013 | Ott et al. | |

FOREIGN PATENT DOCUMENTS

| | | |
|---|---|---|
| EP | 1555031 | 7/2005 |
| WO | WO 2002/053193 | 7/2002 |
| WO | WO 2007/025233 | 3/2007 |
| WO | WO 2007/095192 | 8/2007 |
| WO | WO 2010/091188 | 8/2010 |
| WO | WO 2010/141803 | 12/2010 |
| WO | WO 2011/059808 | 5/2011 |
| WO | 2015/182560 | 12/2015 |
| WO | 2015182560 | 12/2015 |

OTHER PUBLICATIONS

Liao et al., "Effects of decellularization on the mechanical and structural properties of the porcine aortic valve leaflet" Biomaterials, 2008, 29(8):1065-1074.
Sato et al., "Replacement of the left main bronchus with a tissue-engineered prosthesis in a canine model," Ann. Thorac. Surg., 2008, 86:422-428.
Teebken et al., "Tissue engineering of vascular grafts: human cell seeding of decellularised porcine matrix," Eur. J. Vasc. Endovasc. Surg., 2000, 19:381-386.
U.S. Non-Final Office Action in U.S. Appl. No. 13/375,260, dated Feb. 1, 2013, 11 pages.
U.S. Non-Final Office Action in U.S. Appl. No. 13/504,358, dated Dec. 9, 2013, 13 pages.
U.S. Final Office Action in U.S. Appl. No. 13/375,260, dated Oct. 25, 2013, 15 pages.
U.S. Final Office Action in U.S. Appl. No. 13/504,358, dated Jul. 3, 2014, 10 pages.
U.S. Notice of Allowance in U.S. Appl. No. 13/375,260, dated Nov. 26, 2014, 10 pages.
Canadian Office Action in Canadian Application No. 2,762,590, dated Apr. 15, 2016, 13 pages.
Korean Office Action in Korean Application No. 2012-7000278, dated Jul. 14, 2016, 12 pages (with English translation).
U.S. Final Office Action in U.S. Appl. No. 14/559,401, dated Feb. 8, 2017, 11 pages.
Andrade et al., "Cell-based tissue engineering for lung regeneration," Am. J. Physiol. Lung Cell Mal. Physiol., 2007, 292(2):L510-518.
Baptista et al., "Whole Organ Decellularization—A Tool for Bioscaffold Fabrication and Organ," Bioengineering, 31st Annual International Conference of the IEEE EMBS, Sep. 2-6, 2009.
Brew et al., "Mechanical Ventilation Injury and Repair in Extremely and Very Preterm Lungs," PLOS One, 2013, 8(5):e63905.
Chen et al., "Formation of lung alveolar-like structures in collagen-glycosaminoglycan scaffolds in vitro," Tissue Eng., 2005, 11(9-10)1436-1448.
First Chinese Office Action in Chinese Application No. 201080032724.4, dated Dec. 18, 2012, with English translation.
Second Chinese Office Action in Chinese Application No. 201080032724.4, dated Sep. 24, 2013, 9 pages with English translation.
Third Chinese Office Action in Chinese Application No. 201080032724.4, dated May 9, 2014, 8 pages (English translation).
The Decision of Final Rejection of the Application in Chinese Application No. 201080032724.4, Jan. 27, 2015, 7 pages (English translation).
Conconi et al., "Tracheal matrices, obtained by a detergent-enzymatic method, support in vitro the adhesion of chondrocytes and tracheal epithelial cells," Transplant International, 2005, 18:727-734.
Cotiella et al., "Tissue-Engineered Lung: An In Vivo and In Vitro Comparison of Polyglycolic Acid and Pluronic F-127 Hydrogel/Somatic Lung Progenitor Cell Constructs to Support Tissue Growth," Tissue Engineering, 2006, 12:1213-1225.
Declaration of Harald C. Ott, M.D. Under 37 CFR 1.131. and Ott, Curriculum Vitae, Apr. 11, 2014, 17 pages.
Desai et al, "Growth factors in lung development and disease: friends or foe?" Respir. Res., 2002; 3:2.
Ding et al., "Design of compliance chamber and after-load in apparatus for cultured endothelial cells subjected to stresses," Cell Biology International, 2006, 30:439-444.
Gilbert et al., "Decellularization of tissues and organs," Biomaterials, 2006, 27:3675-3683.
Hoganson et al., "Tissue engineering and organ structure: a vascularized approach to liver and lung," Pediatric Research, 2008, 63(5):520-526.
Ichii et al., Current status of islet cell transplantation, J. Hepatobiliary Pancreat. Surg., 2009, 16:101-112.
Ingenito et al., "Design and testing of biological scaffolds for delivering reparative cells to target sites in the lung," J. Tissue Eng. Regen. Med., 2009, 4(4):259-272.
International Preliminary Report on Patentability and Written Opinion in International Application.No. PCT/US2010/037379, dated Dec. 6, 2011, 8 pages.
International Search Report and Written Opinion in International Application No. PCT/US2010/037379, dated Mar. 1, 2011, 9 pages.
International Preliminary Report on Patentability and Written Opinion in International Application No. PCT/US2010/054689, dated May 1, 2012, 9 pages.
International Search Report and Written Opinion in International Application No. PCT/US2010/054689, dated Jul. 11, 2011, 13 pages.
International Search Report in International Application No. PCT/US2010/23213, dated Aug. 12, 2010, 3 pages.
Written Opinion of the International Search Authority in International Application No. PCT/US2010/23213, May 24, 2010, 6 pages.
Japanese Office Action in Japanese Application No. 2012-514170, dated Sep. 16, 2014, 14 pages.
Li et al., "A Single Use, Scalable Perfusion Bioreactor System," BioProcess International, Supplement, 2009.
Liao et al., "Effects of decellularization on the mechanical and structural properties of the porcine aortic valve leaflet," Biomaterials, 2008, 29(8):1065-1074.
Lin et al., "Biocompatibility of Poly-DL-lactic acid (PDLLA) for Lung Tissue Engineering," Journal of Biomaterials Applications, 2006, 21:109-118.

(56) References Cited

OTHER PUBLICATIONS

Macchiarini et al., "Clinical transplantation of a tissue-engineered airway," Lancet, 2008, 372:2023-2030.
Mondrinos et al., "Engineering Three-Dimensional Pulmonary Tissue Constructs," Tissue Engineering, 2006, 12(4):717-728.
Nichols et al., "Engineering of a Complex Organ Progress Toward Development of a Tissue-engineered Lung," Proceedings of the American Thoracic Society, 2008, 5:723-730.
Ott et al., "Regeneration and orthotopic transplantation of a bioartificial lung," Nat Med 2010, 16:927-933.
Ott et al., "Perfusion-decellularized matrix: using nature's platform to engineer a bioartificial heart," Nature Medicine, 2008, 14(2):213-221.
Park et al., "Reprogramming of human somatic cells to pluripotency with defined factors," Nature, 2008, 451:141-146.
Petersen, "In Vitro Development of Engineered Lung Tissue," Duke University Doctoral Dissertation, 2009.
Rey-Santano et al., "Effect of Surfactant and Partial Liquid Ventilation Treatment on Gas Exchange and Lung Mechanics in Immature Lambs: Influence of Gestational Age," PLOS One, 2013, 8:e56127.
Rimensberger, Peter C., "Neonatal respiratory failure," Current Opinion in Pediatrics, 2002, 14:315-321.
Rojanarat et al., "Isoniazid Proliposome Powders for Inhalation—Preparation, Characterization and Cell Culture Studies," International Journal of Molecular Sciences, 2011, 12:4414-4434.
Sato et al., "Replacement of the left main bronchus with a tissue-engineered prosthesis in a canine model," Ann. Thorac. Surg., 2008, 86: 422-428.
Song et al., "Enhanced in vivo function of bioartificial lungs in rats," Ann Thorac Surg., 2011, 92(3):998-1005.
Song et al., "Organ engineering based on decellularized matrix scaffolds," Trends in Molecular Medicine, 2011, 17(8):424-432.
Supplementary Search Report in European Application No. 10784139, dated Aug. 29, 2013, 8 pages.
Takahashi et al., "Induction of pluripotent stem cells from adult human fibroblasts by defined factors," Cell, 2007, 131:861-872.
Teebken et al., "Tissue engineering of vascular grafts: human cell seeding of decellularised porcine matrix," Eur. J. Vase. Endovasc. Surg., 2000, 19:381-386.
Toni et al., "The bioartificial thyroid: a biotechnological perspective in endocrine organ engineering for transplantation replacement," Acta Bio Medica, 2007, 78(Sunn 1):129-155.
US Non-Final Office Action in U.S. Appl. No. 13/375,260, dated Feb. 1, 2013, 11 pages.
US Non-Final Office Action in U.S. Appl. No. 13/504,358, dated Dec. 9, 2013, 13 pages.
US Final Office Action in U.S. Appl. No. 13/375,260, dated Oct. 25, 2013, 15 pages.
US Final Office Action in U.S. Appl. No. 13/504,358, dated Jul. 3, 2014, 10 pages.
US Notice of Allowance in U.S. Appl. No. 13/375,260, dated Nov. 26, 2014, 10 pages.
Vandenbroucke et al., "Regulation of Endothelian Junctional Permeability," Ann. N.Y. Acad. Sci., 2008, 1123:134-145.
Yang et al., "Expression of mutant BMPR-II in pulmonary endothelial cells promotes apoptosis and a release of factors that stimulate proliferation of pulmonary arterial smooth muscle cells," Pulmonary Circulation, 2011, 1(1):103-110.
Yu et al., "Induced pluripotent stem cell lines derived from human somatic cells," Science, 2007, 318:1917-1920.
Zhu et al., "Partial liquid ventilation decreases tissue and serum tumor necrosis factor-a concentrations in acute lung injury model of immature piglet induced by oleic acid," Chinese Medical Journal, 2012, 125(1):123-128.

\* cited by examiner

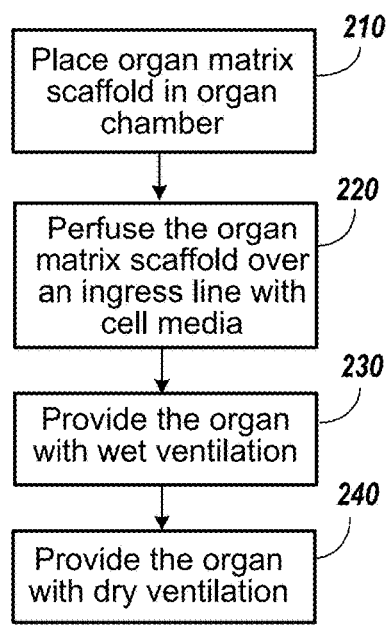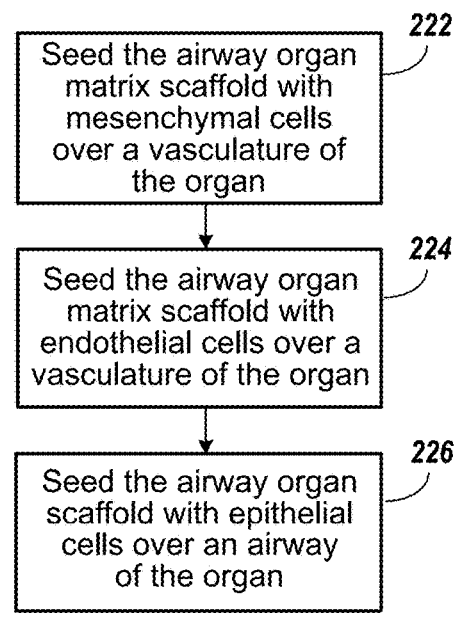
FIG. 2A
FIG. 2B

BIOARTIFICAL LUNG

CROSS REFERENCE TO RELATED APPLICATIONS

This application is a continuation of U.S. patent application Ser. No. 13/375,260, filed Feb. 24, 2012, which is a 371 of International Application No. PCT/2010/037379, filed Jun. 4, 2010, and claims benefit to U.S. Provisional Application No. 61/184,170, filed on Jun. 4, 2009 and U.S. Provisional Application No. 61/256,281, flied on Oct. 29, 2009, the contents of which are incorporated herein in their entirety.

TECHNICAL FIELD

This document provides an apparatus and methods related to tissue generation. For example, this document provides methods for generating transplantable lung tissue in a human or animal subject.

BACKGROUND

Lung transplants represent a final hope for many patients experiencing conditions typified by lung failure, e.g., Chronic obstructive pulmonary disease (COPD) COPD, Cystic Fibrosis, lung cancers, and congenital lung diseases, among others. Typical wait time for a lung transplant can be two years or more, resulting in a 30% mortality rate for those on the waiting list.

SUMMARY

Presented is an airway organ bioreactor apparatus. The apparatus has an organ chamber configured to hold an organ matrix scaffold onto which a cell media is perfused to grow an organ. The apparatus further has a wet ventilator system configured to supply a wet ventilation to the organ via the first branch of the connector. The apparatus further has a dry ventilator system configured to supply a dry ventilation to the organ via the first branch of the connector. The apparatus further has a controller configured to control the delivery of wet ventilation or delivery of dry ventilation.

The apparatus can further comprise a connector including a first branch, a second branch, and a third branch connected to the organ. The apparatus further has a first three-way junction at which the first branch of the connector and the second branch of the connector are connected with the third branch of the connector. The three-way junction including a switch can be configured to toggle between the first branch and the second branch. The apparatus further has a wet ventilator system configured to supply a wet ventilation to the organ via the first branch of the connector. The apparatus further has a dry ventilator system configured to supply a dry ventilation to the organ via the second branch of the connector. The apparatus further has a controller configured to control the switch of the first three-way junction, thereby controlling delivery of wet ventilation or delivery of dry ventilation.

The apparatus can further comprise a reservoir system configured to supply cell media to the organ over an ingress line; and drain waste media from the organ over an egress line, the egress line including a first branch, a second branch, and a third branch; and a second three-way junction at which the first branch of the egress line and the second branch of the egress line are connected with the third branch of the egress line. The wet ventilator system can comprise a wet ventilator connected to the organ chamber via a wet ventilation line; and a compliance chamber connected to the organ via the first branch of the connector. A wet positive and expiratory pressure (wPEEP) can be provided to the organ chamber via an elevation of the compliance chamber. The apparatus can further comprise an afterload chamber connected to the organ chamber via the second branch of the egress line; and the reservoir system via an egress return line. The reservoir system can comprise a first reservoir connected to the organ chamber via an ingress line; and a second reservoir connected to the organ chamber via an organ chamber drain; and the afterload chamber via the egress return line, wherein the first reservoir and second reservoir circulate media over a reservoir feed line and a reservoir drain. The dry ventilator system can comprise a dry ventilation chamber including a nebulizer, connected to the organ via the second branch of the connector; and a first dry ventilator configured to provide a dry positive and expiratory pressure (dPEEP) to the organ chamber and connected to the dry ventilation chamber via a dPEEP line. The dry ventilator system can further comprise a second dry ventilator connected to the organ chamber via a dry ventilator line. The apparatus can further comprise a gas tank configured to supply gaseous media to the organ chamber, the dry ventilation chamber, and the reservoir system. The controller can be operated by a computer.

In another aspect, this document features a method of providing a bioartificial airway organ. The method can comprise providing a lung tissue matrix comprising a lung tissue matrix and substantial vasculature; seeding the lung tissue matrix with cells; providing the organ with wet ventilation for a time sufficient for a first desired degree of organ maturation to occur; and providing the wet-matured organ with dry ventilation for a time sufficient for a second desired degree of organ maturation to occur, thereby providing a bioartificial lung. The method can further comprise seeding the lung tissue matrix with endothelial cells over the vasculature of the organ; and seeding the airway lung tissue matrix with epithelial cells over an airway of the organ. The method can further comprise seeding the lung tissue matrix with stem cells over a vasculature of the organ. The stem cells can be bone marrow derived mesenchymal stem cells or induced pluripotent stem (iPS) cells. The stem cells can be suspended in a fluid at a concentration of about 100 million cells per 30 cc of fluid. The endothelial cells can be suspended in a fluid at a concentration of about 100 million cells per 10 cc of fluid. The epithelial cells can be suspended in a fluid at a concentration of about 100 million cells per 5 cc of fluid. The method can further comprise monitoring the degree of organ maturation until the first desired degree of organ maturation has occurred; stopping the providing of the wet ventilation to the organ; applying an artificial surfactant to the organ; and starting the providing of the dry ventilation to the organ. Providing the lung tissue matrix with wet ventilation can comprise connecting the airway to a wet ventilator via a wet ventilator line; connecting the organ to a compliance chamber via a wet ventilation line; increasing a wet airway pressure over the wet ventilation line; and providing a wet positive and expiratory pressure (wPEEP) to the organ by elevating the compliance chamber. The wet ventilation is provided at a physiologic tidal volume. Providing the wet-matured organ with dry ventilation can comprise connecting the airway to a dry ventilation chamber via a dry ventilation line; connecting the dry ventilation chamber to a first dry ventilator over a dry positive and expiratory pressure (dPEEP) line; increasing a dry airway pressure over the dry ventilation line; disconnecting the wet ventilation line; and connecting the organ to a second dry ventilator via a dry ventilator line. The lung tissue matrix can comprise decellularized human lung tissue or an artificial lung matrix. The bioartificial lung can comprise a sufficient number of cells to provide full lung function or a fraction thereof.

In another aspect, this document features a bioartificial lung produced by the method provided herein. The bioartificial lung can be a full lung or a portion thereof.

In a further aspect, this document features a method of treating a subject having impaired or reduced lung capacity. The method can comprise transplanting the bioartificial lung into the subject.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A, 2B, 2C, and 2D are flow charts of an exemplary method for growing lung tissue in a lung bioreactor.

DETAILED DESCRIPTION

Figure 1:
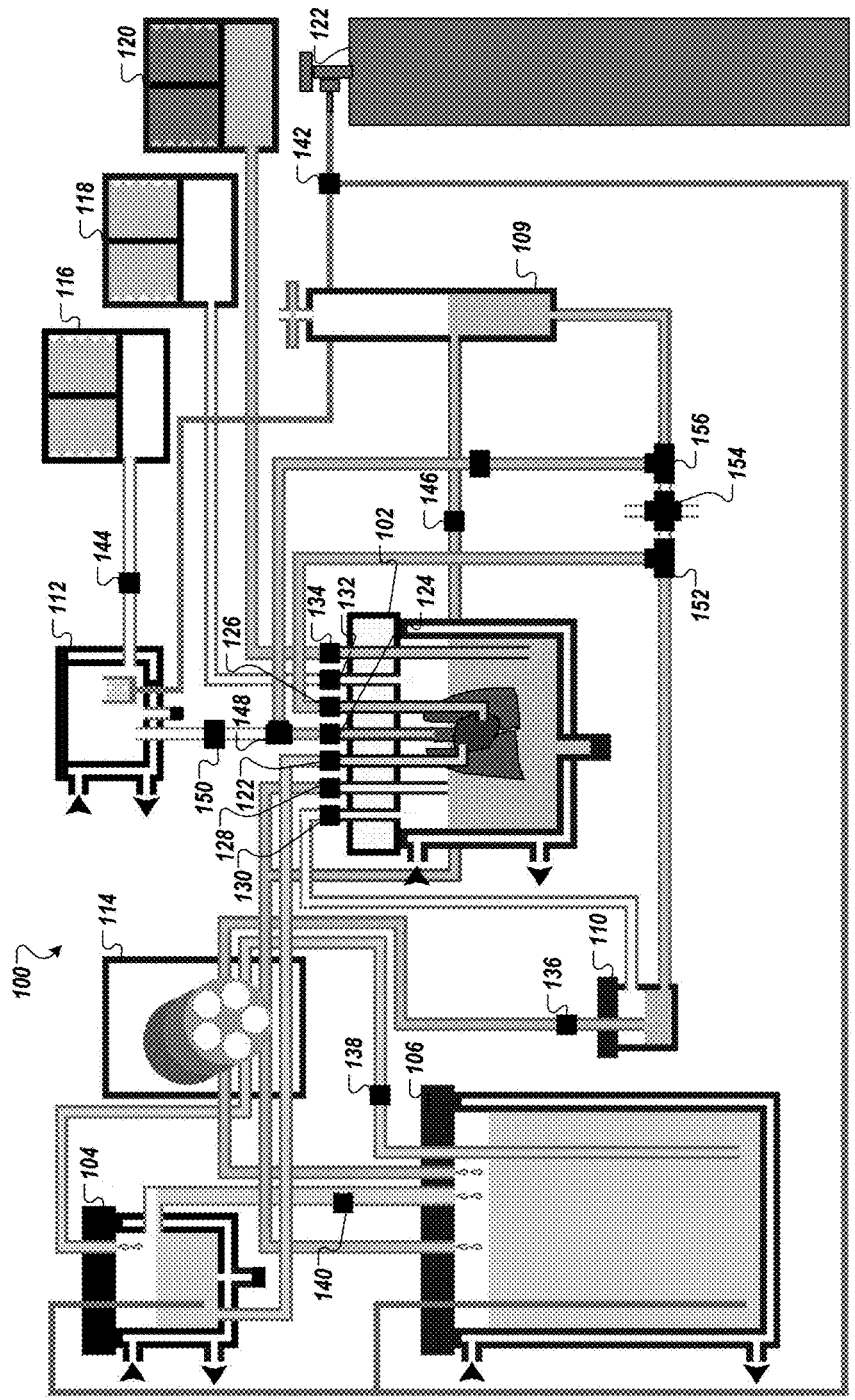
FIG. 1 is a schematic diagram of an exemplary lung bioreactor.

This document relates to methods and materials involved, in organ generation. The present invention is based, at least in part, on the discovery of bioreactors configured to generate functional lung tissue that can be used to provide a more realistic environment for growth of functional airway organs ready for transplantation into humans and other animals. The lung tissue is generated over a given matrix, e.g., an artificial or decellularized lung tissue matrix.

As used herein, a "functional" lung tissue performs most or all of the functions of a normal healthy lung, e.g., allows for transportation of oxygen from the air into the bloodstream, and the release of carbon dioxide from the bloodstream into the air. It humidifies the inhaled air, produces surfactant to decrease surface tension in the alveoli and produces and transports mucus to remove inhaled particulate matter from the distal to the proximal airway.

As used herein, the terms "decellularized" and "acellular" are used interchangeably and are defined as the complete or near complete absence of detectable intracellular, endothelial cells, epithelial cells, and nuclei in histologic sections using standard histological staining procedures. Preferably, but not necessarily, residual cell debris also has been removed from the decellularized organ or tissue.

Decellularized Tissue/Organ Matrices

Methods and materials for a preparing a decellularized lung tissue matrix are known in the art. Any appropriate materials can be used to prepare such a matrix. In a preferred embodiment, a tissue matrix can be an acellular tissue scaffold developed from decellularized lung tissue. For example, tissue such as human lungs, or a portion thereof, can be decellularized by an appropriate method to remove native cells from the tissue while maintaining morphological integrity and vasculature of the tissue or tissue portion and preserving extracellular matrix (ECM) proteins. In some cases, cadaveric lungs, or portions thereof, can be used. Decellularization methods can include subjecting tissue (e.g., lung tissue) to repeated freeze-thaw cycles using liquid nitrogen. In other cases, a tissue can be subjected to an anionic or ionic cellular disruption medium such as sodium dodecyl sulfate (SDS), polyethylene glycol (PEG), or TritonX-100. The tissue can also be treated with a nuclease solution (e.g., ribonuclease, deoxyribonuclease) and washed in sterile phosphate buffered saline with mild agitation. In some cases, decellularization can be performed by cannulating the vessels, ducts, and/or cavities of the organ or tissue using methods and materials known in the art. Following the cannulating step, the organ or tissue can be perfused via the cannula with a cellular disruption medium as described above. Perfusion through the tissue can be antegrade or retrograde, and directionality can be alternated to improve perfusion efficiency. Depending upon the size and weight of an organ or tissue and the particular anionic or ionic detergent(s) and concentration of anionic or ionic detergent(s) in the cellular disruption medium, a tissue generally is perfused from about 2 to about 12 hours per gram of tissue with cellular disruption medium. Including washes, an organ may be perfused for up to about 12 to about 72 hours per gram of tissue. Perfusion generally is adjusted to physiologic conditions including flow rate and pressure.

Decellularized tissue can consist essentially of the extracellular matrix (ECM) component of all or most regions of the tissue, including ECM components of the vascular tree. ECM components can include any or all of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. In a preferred embodiment, decellularized lung tissue matrix retains a substantially intact vasculature. Preserving a substantially intact vasculature enables connection of the tissue matrix to a subject's vascular system upon transplantation. In addition, a decellularized tissue matrix can be further treated with, for example, irradiation (e.g., UV, gamma) to reduce or eliminate the presence of any type of microorganism remaining on or in a decellularized tissue matrix.

Methods for obtaining decellularized tissue matrices using physical, chemical, and enzymatic means are known in the art, see, e.g., Liao et al, *Biomaterials* 29(8):1065-74 (2008); Gilbert et al., *Biomaterials* 27(9):3675-83 (2006); Teebken et al., *Eur. J. Vasc. Endovasc. Surg.* 19:381-86 (2000). See also U.S. Pat. Publication Nos. 2009/0142836; 2005/0256588; 2007/0244568; and 2003/0087428.

Artificial Organ Matrices

Methods and materials for a preparing an artificial organ matrix are known in the art. Any appropriate materials can be used to prepare such a matrix. In a preferred embodiment, an artificial organ matrix can be a scaffold developed from porous materials such as, for example, polyglycolic acid, Pluronic F-127 (PF-127), Gelfoam sponge, collagen-glycosaminoglycan (GAG), fibrinogen-fibronectin-vitronectin hydrogel (FFVH), and elastin. See, e.g., Ingenito et al., *J Tissue Eng Regen Med.* 2009 Dec. 17; Hoganson et al., *Pediatric Research*, May 2008, 63(5):520-526; Chen et al., *Tissue Eng.* 2005 September-October; 11(9-10):1436-48. In some cases, an artificial organ matrix can have porous structures similar to alveolar units. See Andrade et al., *Am J Physiol Lung Cell Mol. Physiol.* 2007 February; 292(2): L510-8. In some cases, an implanted artificial organ matrix can express organ-specific markers (e.g., lung-specific markers for Clara cells, pneumocytes, and respiratory epithelium). In some cases, an implanted artificial organ matrix can organize into identifiable structures (e.g., structures similar to alveoli and terminal bronchi in an artificial lung matrix). For example, an implanted artificial lung maxtrix made using FFVH can promote cell attachment, spreading and extracellular matrix expression in vitro and apparent engraftment in vivo, with evidence of trophic effects on the surrounding tissue. See Ingenito et al., supra. See also U.S. Pat. Nos. 7,662,409 and 6,087,552; United States Patent Publication Nos. 2010/0034791; 2009/0075282; 2009/0035855; 2008/0292677; 2008/0131473; 2007/0059293; 2005/0196423; 2003/0166274; 2003/0129751; 2002/0182261; 2002/0182241; and 2002/0172705.

Cell Seeding

In the methods described herein, a lung tissue matrix, e.g., decellularized lung tissue matrix or artificial lung matrix, is seeded with cells, e.g., differentiated or regenerative cells.

Any appropriate regenerative cell type, such as naïve or undifferentiated cell types, can be used to seed the lung tissue matrix. As used herein, regenerative cells can include, without limitation, progenitor cells, precursor cells, and "adult"-derived stem cells including umbilical cord cells (e.g., human umbilical vein endothelial cells) and fetal stem cells. Regenerative cells also can include differentiated or committed cell types. Stem cells appropriate for the methods and materials provided herein can include human induced pluripotent stem cells (iPSC), mesenchymal stem cells, human umbilical vein endothelial cells, multipotent adult progenitor cells (MAPC), or embryonic stem cells. In some cases, regenerative cells derived from other tissues also can be used. For example, regenerative cells derived from skin, bone, muscle, bone marrow, synovium, or adipose tissue can be used to develop stem cell-seeded tissue matrices.

In some cases, a lung tissue matrix provided herein can be further seeded with differentiated cell types such as human epithelial cells and endothelial cells. For example, a lung matrix can be seeded with endothelial cells via the vasculature, and epithelial and mesenchymal cells, and human umbilical vein endothelial cells (HUVEC) through perfusion seeding.

Any appropriate method for isolating and collecting cells for seeding can be used. For example, induced pluripotent stem cells generally can be obtained from somatic cells "reprogrammed" to a pluripotent state by the ectopic expression of transcription factors such as Oct4, Sox2, Klf4, c-MYC, Nanog, and Lin28. See Takahashi et al., *Cell* 131:861-72 (2007); Park et al., *Nature* 451:141-146 (2008); Yu et al., *Science* 318:1917-20 (2007). Cord blood stem cells can be isolated from fresh or frozen umbilical cord blood. Mesenchymal stem cells can be isolated from, for example, raw unpurified bone marrow or ficoll-purified bone marrow. Epithelial and endothelial cells can be isolated and collected from living or cadaveric donors, e.g., from the subject who will be receiving the bioartificial lung, according to methods known in the art. For example, epithelial cells can be obtained from a skin tissue sample, and endothelial cells can be obtained from a vascular tissue sample. In some embodiments, proteolytic enzymes are perfused in to the tissue sample through a catheter placed in the vasculature. Portions of the enzymatically treated tissue can be subjected to further enzymatic and mechanical disruption. The mixture of cells obtained in this manner can be separated to purify epithelial and endothelial cells. In some cases, flow cytometry-based methods (e.g., fluorescence-activated cell sorting) can be used to sort cells based on the presence or absence of specific cell surface markers. In cases where non-autologous cells are used, the selection of immune type-matched cells should be considered, so that the organ or tissue will not be rejected when implanted into a subject.

Isolated cells can be rinsed in a buffered solution (e.g., phosphate buffered saline) and resuspended in a cell culture medium. Standard cell culture methods can be used to culture and expand the population of cells. Once obtained, the cells can be contacted with a tissue matrix to seed the matrix. For example, a tissue matrix can be seeded with at least one cell type in vitro at any appropriate cell density. For example, cell densities for seeding a matrix can be at least $1 \times 10^3$ cells/gram matrix. Cell densities can range between about $1 \times 10^5$ to about $1 \times 10^{10}$ cells/gram matrix (e.g., at least 100,000, 1,000,000, 10,000,000, 100,000,000, 1,000,000,000, or 10,000,000,000 cells/gram matrix) can be used.

In some cases, a decellularized or artificial lung tissue matrix as provided herein can be seeded with the cell types and cell densities described above by perfusion seeding. For example, a flow perfusion system can be used to seed the decellularized lung tissue matrix via the vascular system preserved in the tissue matrix. In some cases, automated flow perfusion systems can be used under the appropriate conditions. Such perfusion seeding methods can improve seeding efficiencies and provide more uniform distribution of cells throughout the composition. Quantitative biochemical and image analysis techniques can be used to assess the distribution of seeded cells following either static or perfusion seeding methods.

In some cases, a tissue matrix can be impregnated with one or more growth factors to stimulate differentiation of the seeded regenerative cells. For example, a tissue matrix can be impregnated with growth factors appropriate for the methods and materials provided herein, for example, vascular endothelial growth factor (VEGF), TGF-β growth factors, bone morphogenetic proteins (e.g., BMP-1, BMP-4), platelet derived growth factor (PDGF), basic fibroblast growth factor (b-FGF), e.g., FGF-10, insulin-like growth factor (IGF), epidermal growth factor (EGF), or growth differentiation factor-5 (GDF-5). See, e.g., Desai and Cardoso, *Respir. Res.* 3:2 (2002).

Seeded tissue matrices can be incubated for a period of time (e.g., from several hours to about 14 days or more) post-seeding to improve fixation and penetration of the cells in the tissue matrix. The seeded tissue matrix can be maintained under conditions in which at least some of the regenerative cells can multiply and/or differentiate within and on the acellular tissue matrix. Such conditions can include, without limitation, the appropriate temperature and/or pressure, electrical and/or mechanical activity (e.g., ventilation), force, the appropriate amounts of $O_2$ and/or $CO_2$, an appropriate amount of humidity, and sterile or near-sterile conditions. Such conditions can also include wet ventilation, wet to dry ventilation and dry ventilation. In some cases, nutritional supplements (e.g., nutrients and/or a carbon source such as glucose), exogenous hormones, or growth factors can be added to the seeded tissue matrix. Histology and cell staining can be performed to assay for seeded cell propagation. Any appropriate method can be performed to assay for seeded cell differentiation. In general, the methods described herein will be performed in an airway organ bioreactor apparatus, e.g., as described herein.

Thus the methods described herein can be used to generate a transplantable bioartificial lung tissue, e.g., for transplanting into a human subject. As described herein, a transplantable tissue will preferably retain a sufficiently intact vasculature that can be connected to the patient's vascular system.

The bioartificial lung tissues described herein can be combined with packaging material to generate articles of manufacture or kits. Components and methods for producing articles of manufacture are well known. In addition to the bioartificial tissues, an article of manufacture or kit can further can include, for example, one or more anti-adhesives, sterile water, pharmaceutical carriers, buffers, and/or other reagents for promoting the development of functional lung tissue in vitro and/or following transplantation. In addition, printed instructions describing how the composition contained therein can be used can be included in such articles of manufacture. The components in an article of manufacture or kit can be packaged in a variety of suitable containers.

Methods for Using Bioartificial Lungs

This document also provides methods and materials for using bioartificial lung tissues and, in some cases, promoting lung function. In some embodiments, the methods provided herein can be used to restore some lung function in patients having diseases that impair or reduce lung capacity (e.g., cystic fibrosis, COPD, emphysema, lung cancer, asthma, lung trauma, or other genetic or congenital lung abnormalities, e.g., bronchogenic cyst, pulmonary agenesis and hypoplasia, polyalveolar lobe, alveolocapillary dysplasia, sequestration including arteriovenous malformation (AVM) and scimitar syndrome, pulmonary lymphangiectasis, congenital lobar emphysema (CLE), and cystic adenomatoid malformation (CAM) and other lung cysts). The methods provided herein also include those wherein the subject is identified as in need of a particular stated treatment, e.g., increased lung function, or increased or improved lung capacity.

Bioartificial lung tissues (e.g., whole organs or portions thereof) can be generated according to the methods provided herein. In some embodiments, the methods comprise transplanting a bioartificial lung tissue as provided herein to a subject (e.g., a human patient) in need thereof. In some embodiments, a bioartificial lung tissue is transplanted to the site of diseased or damage tissue. For example, bioartificial lung tissues can be transplanted into the chest cavity of a subject in place of (or in conjunction with) a non-functioning or poorly-functioning lung; methods for performing lung transplantation are known in the art, see, e.g., Boasquevisque et al., Surgical Techniques: Lung Transplant and Lung Volume Reduction, Proceedings of the American Thoracic Society 6:66-78 (2009); Camargo et al., Surgical maneuvers for the management of bronchial complications in lung transplantation, Eur J Cardiothorac Surg 2008; 34:1206-1209 (2008); Yoshida et al., "Surgical Technique of Experimental Lung Transplantation in Rabbits," *Ann Thorac Cardiovasc Surg.* 11(1):7-11 (2005); Venuta et al., Evolving Techniques and Perspectives in Lung Transplantation, Transplantation Proceedings 37(6):2682-2683 (2005); Yang and Conte, *Transplantation Proceedings* 32(7):1521-1522 (2000); Gaissert and Patterson, Surgical Techniques of Single and Bilateral Lung Transplantation in The Transplantation and Replacement of Thoracic Organs, 2d ed. Springer Netherlands (1996).

The methods can include transplanting a bioartificial lung or portion thereof as provided herein during a surgical procedure to partially or completely remove a subject's lung and/or during a lung resection. In some cases, the methods provided herein can be used to replace or supplement lung tissue and function in a subject, e.g., a human or animal subject.

Any appropriate method(s) can be performed to assay for lung function before or after transplantation. For example, methods can be performed to assess tissue healing, to assess functionality, and to assess cellular in-growth. In some cases, tissue portions can be collected and treated with a fixative such as, for example, neutral buffered formalin. Such tissue portions can be dehydrated, embedded in paraffin, and sectioned with a microtome for histological analysis. Sections can be stained with hematoxylin and eosin (H&E) and then mounted on glass slides for microscopic evaluation of morphology and cellularity. For example, histology and cell staining can be performed to detect seeded cell propagation. Assays can include functional evaluation of the transplanted tissue matrix or imaging techniques (e.g., computed tomography (CT), ultrasound, or magnetic resonance imaging (e.g., contrast-enhanced MRI)). Assays can further include functional tests under rest and physiologic stress (e.g., body pletysmography, lung function testing). Functionality of the matrix seeded with cells can be assayed using methods known in the art, e.g., histology, electron microscopy, and mechanical testing (e.g., of volume and compliance). Gas exchange can be measured as another functionality assay. To assay for cell proliferation, thymidine kinase activity can be measured by, for example, detecting thymidine incorporation. In some cases, blood tests can be performed to evaluate the function of the lungs based on levels of oxygen in the blood.

In some cases, molecular biology techniques such as RT-PCR can be used to quantify the expression of metabolic and differentiation markers. Any appropriate RT-PCR protocol can be used. Briefly, total RNA can be collected by homogenizing a biological sample (e.g., tendon sample), performing a chloroform extraction, and extracting total RNA using a spin column (e.g., RNeasy® Mini spin column (QIAGEN, Valencia, Calif.)) or other nucleic acid-binding substrate. In other cases, markers associated with lung cells types and different stages of differentiation for such cell types can be detected using antibodies and standard immunoassays.

Airway Organ Bioreactor Apparatus

An exemplary airway organ bioreactor apparatus is presented in FIG. 1. Throughout the specification, a lung will be offered as an example of an airway organ. Other examples can include, e.g., a trachea.

Referring to FIG. 1, components of the bioreactor include a lung chamber 102, an airway connector including a tracheal line 124, a wet ventilation line 150, and a dry ventilation line 134, wet ventilator system 120, dry ventilator system 116 and 118, three-way connector 148 at the junction between the tracheal line 124, wet ventilation line 150, and dry ventilation line 134, and controller (not shown). The controller is computer-operated, but also be operated manually. The bioreactor can also include a pulmonary arterial line 122, a pulmonary venous line 126, a reservoir system 104 and 106, a roller pump 114, a gas tank 122 and accompanying gas lines, an afterload chamber 110, a pulmonary venous return line 136, and a lung chamber pressure line 128. The bioreactor further includes a compliance chamber 109 and compliance chamber drain 146. The bioreactor can further include a membrane oxygenator in addition or instead to provide oxygenation and carbonation of perfusing media solutions (not shown).

Lung chamber 102 holds a decellularized lung matrix scaffold. Lung chamber 102 is closed to provide a sterile lung culture environment. The pulmonary artery of the lung matrix is connected to pulmonary arterial line 122 and the pulmonary vein of the lung matrix is connected to pulmonary arterial vein 126, each via vascular cannulas. The trachea of the lung matrix is connected to the airway connector via the tracheal line 124.

Within lung chamber 102, the cell matrix is perfused antegradely with a cell media in order to allow seeding of cells to grow the lung. The perfusion takes place over pulmonary arterial line 122 to the pulmonary artery. From there, media flows through the pulmonary vasculature and flows out to the reservoir system (104 and 106).

Reservoir system includes a first reservoir 104 and a second reservoir 106, as well as a reservoir feeding line 140 and a reservoir drain (140). Cell media circulates between the reservoirs 104 and 106 through reservoir feeding line 138 and reservoir drain 140. A microfilter can optionally be placed in feeding line 140 for sterile filtration. Cell media is also oxygenated in reservoirs 104 and 106. For perfusion, the cell media is fed from reservoir 104 through the pulmonary arterial line 122 via roller pump 114 or via gravity to the pulmonary artery.

The media that flows out to reservoir 106 is aspirated directly from lung chamber 102 via lung chamber drain (4) to maintain a constant fluid level within the lung chamber 102. The media that flows out of the lung via the third connector 126 drains to the afterload chamber 110 via gravity and is aspirated via the afterload chamber drain 136 to the reservoir 106. Afterload chamber 110 is connected to the lung chamber 102 via the lung chamber pressure line 130 and the reservoir 106 via pulmonary venous return line 136. The lung chamber pressure line equilibrates the pressures in lung chamber 102 and afterload chamber 110. Afterload chamber 110 is also connected to the lung chamber 102 via the trachea and wet ventilation line through three-way junction 156.

One exemplary method of reintroducing cells into the matrix is as follows. During a perfusion of the lung matrix, a cellularization of the matrix begins. About 100 million mesenchymal cells suspended in about 30 cc of media are seeded via pulmonary arterial line 122. The mesenchymal cells are bone marrow derived embryo stem cells, but can also be e.g., iPS or hematopoietic cells as described in U.S. Ser. No. 12/233,017, "Generation of Inner Ear Cells," the contents of which are incorporated in their entirety by reference. In some embodiments, upon completion of the seeding, the perfusion is stopped, e.g., for about 60 minutes, to allow for cell attachment. During the stoppage of the perfusion, cell media is drained from the trachea and pulmonary vein; the drained cell media then flows to reservoir 106. After the 60 minute stoppage, the perfusion with media alone is continued, e.g., for about 24 hours. To maintain constant media level in compliance chamber 109, it can be connected to reservoir 104 via an additional line (not shown).

Next, conditions are set up for seeding of endothelial cells. The tracheal line 124 is connected to the wet ventilation line 150 via the three-way junction 148 and its controller. The three-way junction 156 is turned, using its controller, to connect the wet ventilation line 150 to the compliance chamber 109. Compliance chamber 109 provides positive wet airway pressure (wAP) to limit net media flow through interstitial space and the trachea while limiting airway pressure to a physiologic range. The wAP is adjusted through an adjustment of the chamber 109. As a result, a portion of the cell media drains through the pulmonary venous line (3) to reservoir 106, while a smaller portion of the cell media drains via lymphatics through lung chamber drain line 128 to reservoir 106.

About 100 million endothelial cells suspended in about 15 cc of media are seeded through pulmonary arterial line 122 via about 10 minutes of gravity feeding. Upon completion of the seeding, the perfusion is stopped, e.g., for about 60 minutes to allow for cell attachment. After the stoppage, the perfusion is continued, e.g., for about 3-5 days to allow for a formation of an endothelial cell monolayer.

After endothelial cells have been seeded and the endothelial cell monolayer has been formed, epithelial cells are ready to be seeded. For seeding of epithelial cells, the three-way junction 156 is turned, using its controller, to occlude wet ventilation line 150. About 200 million epithelial cells suspended in about 15 cc of media are seeded through tracheal line 124 into the trachea. In some embodiments, the epithelial cells are pneumocytes. Upon completion of the seeding, perfusion via the pulmonary artery is stopped, e.g., for about 60 minutes.

Also, once cell seeding of the lung has been completed, wet ventilation is needed to advance cell suspension into the peripheral airways. Wet ventilator system 120 provides wet ventilation to the lung over wet ventilation line 150.

Three-way junction 156 is turned, using its controller, to connect wet ventilation line 150 to compliance chamber 109. The wAP is increased to provide a small flow into the interstitial space and increase cell attachment. Wet ventilation is provided to the lung for about 5 minutes, held for about 60 minutes, then provided to the lung for about another 5 minutes, and then held for about 24 hours. The wet ventilation is provided at physiologic tidal volume (about 500 mL for a human) while at a reduced rate to keep wet peak inspiratory and expiratory pressure low. A wet positive and expiratory pressure is provided via elevation of compliance chamber 109.

Once perfusion is resumed, antegrade perfusion and wet ventilation are provided for a period of about 5 days to enable tissue formation.

A switch from wet to dry ventilation is made after the about 5 day period or after a monitor (not shown) determines that the lung has reached sufficient maturity. Artificial surfactant is administered via tracheal line 124. Then three-way junction 148 is turned, using its controller, so that the tracheal line 124 is connected to dry ventilation line 134 and dry ventilation system (116 and 118). Dry ventilation system includes dry ventilation chamber 112 having a nebulizer (not shown) for providing humidified air, first dry ventilator 116, and second dry ventilator 118. Dry ventilation chamber 112 is connected to first dry ventilator 116 via a dry PEEP line 144 and to the tracheal line via the dry ventilation line 134. This way, the lung is ventilated to slowly fill its airspace with gas rather than fluid. The gas used is carbogen supplied via gas line by gas tank 122. Dry ventilator 116 is configured to provide a dPEEP to dry ventilation chamber 112 and subsequently enable fluid drainage in lung chamber 102. Next, wet ventilation system 120 is discontinued and dry ventilator 118 is opened to the lung chamber in order to increase ventilation rate to the physiologic rate, empty lung chamber 102 of fluid, and surround lung with humidified air within lung chamber 102. After about 3 days of tissue maturation, a perfusate gas analysis is performed to confirm formation of functional tissue and that the lung can be removed from the bioreactor.

In switching between the wet ventilation and dry ventilation, the lung develops under conditions simulating the conditions under which a lung develops naturally. It has been determined that this environment is necessary for lung development, and that the bioreactor as described provides system and methods needed to generate tissue engineered lungs for transplantation.

An exemplary method of cellularizing a lung matrix is illustrated in FIG. 2A. A lung matrix is placed 210 into the lung chamber. The lung matrix is then perfused 220 with a cell media over a pulmonary arterial line. The lung matrix is then provided 230 with wet ventilation. Finally, the lung matrix is provided with dry ventilation 240.

During perfusion 220 of the lung matrix, as illustrated in FIG. 2B, the lung matrix is seeded 222 with mesenchymal or other stem cells over the vasculature of the lung. The lung matrix is then seeded 224 with endothelial cells over the vasculature of the lung. The lung matrix is then seeded 226 with epithelial cells over the lung airway.

Figure 2C:
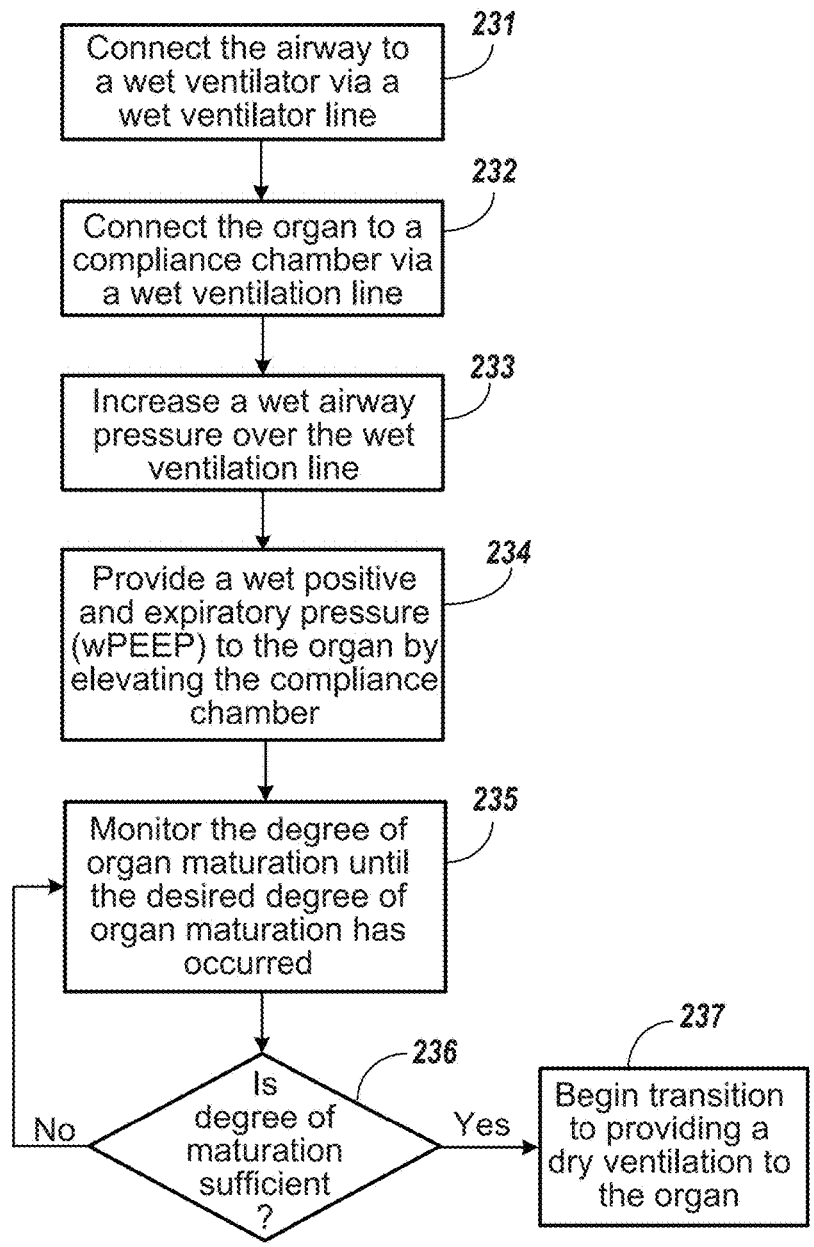

To provide the wet ventilation, as illustrated in FIG. 2C, the lung airway is connected 231 to a wet ventilator over a wet ventilator line. The lung is then connected 232 to a compliance chamber via a wet ventilation line. By adjusting the height of a fluid within the compliance chamber, a wet airway pressure is then increased 233 over the wet ventilation line. Further, by elevating the compliance chamber, a wet PEEP (wPEEP) is then provided 234. A degree of maturation of the lung growing on the lung matrix is monitored 235. If the degree of maturation is determined 236 to be acceptable, then a transition to a dry ventilation is begun 237.

Figure 2D:
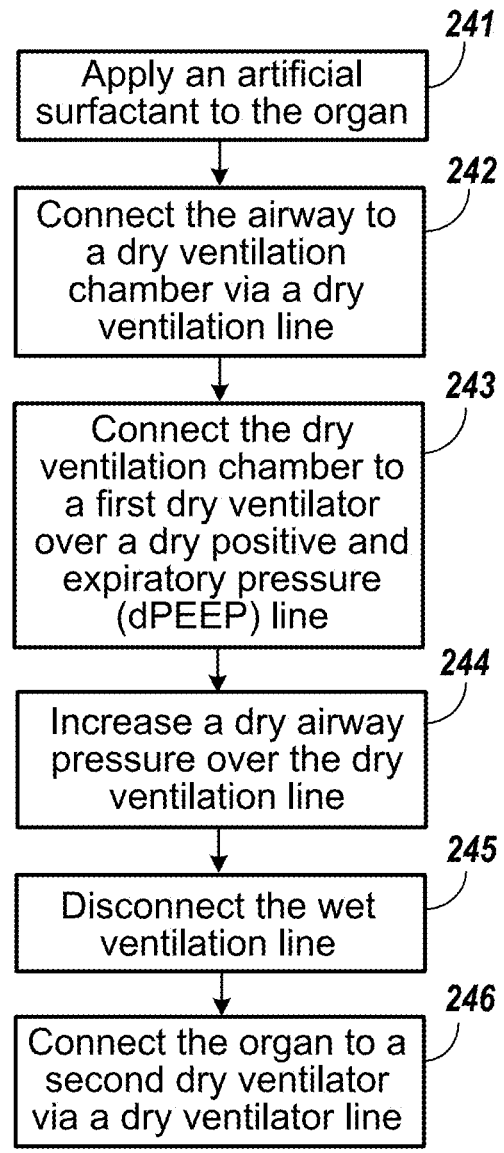

To provide the dry ventilation, as illustrated in FIG. 2D, an artificial surfactant is applied 241 through the trachea. The trachea is then connected 242 to a dry ventilation chamber via a dry ventilation line. The dry ventilation chamber is connected 243 to a first dry ventilator over a dPEEP line. A dry airway pressure is then increased 244 over the dry ventilation line. The wet ventilation line is 245 disconnected, and the lung chamber is connected 246 to a second dry ventilator.

A complete rat lung may require, in total, between about 200 and about 400 million cells. Extrapolation to human provides an estimate of between about 20 and about 40 billion cells for a complete lung. Such a number of cells to generate may require more time than a patient may have. A patient that requires a percentage of lung function, say, 20%, would only need about 20% of this number and would have to wait proportionally less time for a new lung.

Figure 3:
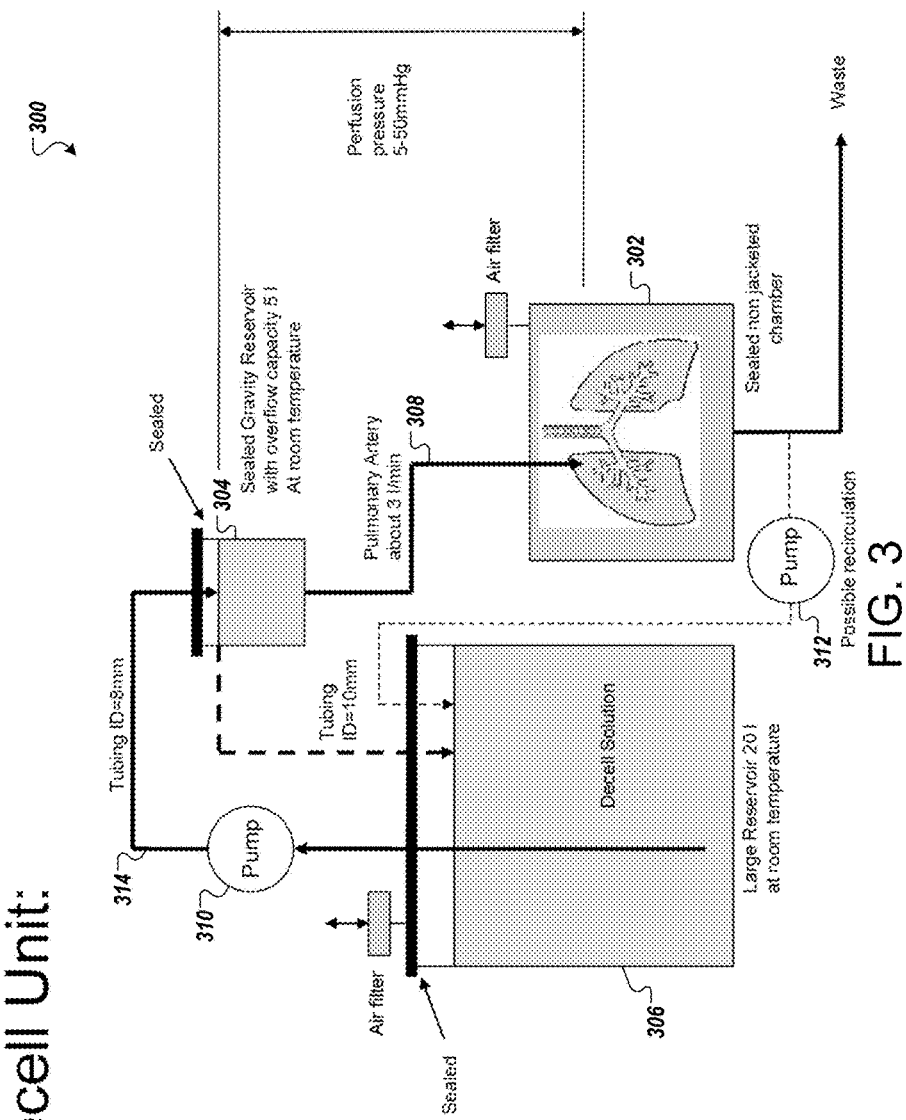
FIG. 3 is a schematic drawing of an exemplary lung decellularization unit.

An exemplary airway organ bioreactor apparatus for use in organ decellularization is presented in FIG. 3. As described above, a lung will be offered as an example of an airway organ. Referring to FIG. 3, components of the bioreactor include lung chamber 302, sealed gravity reservoir 304, and large reservoir 306, where reservoirs 304 and 306 contain decellularization solution for perfusion into the lung in lung chamber 302. Decellularization solution circulates between the reservoirs 304 and 306 through a reservoir feeding line 314. The pulmonary artery of the lung matrix is connected to pulmonary arterial line 308 through which decellularization solution is perfused into lung tissue via gravity flow from reservoir 304. Following decellularization, waste is removed from lung chamber 302. In some cases, solution from lung chamber 302 is recirculated via pump 312 which feeds into reservoir 306.

Figure 4:
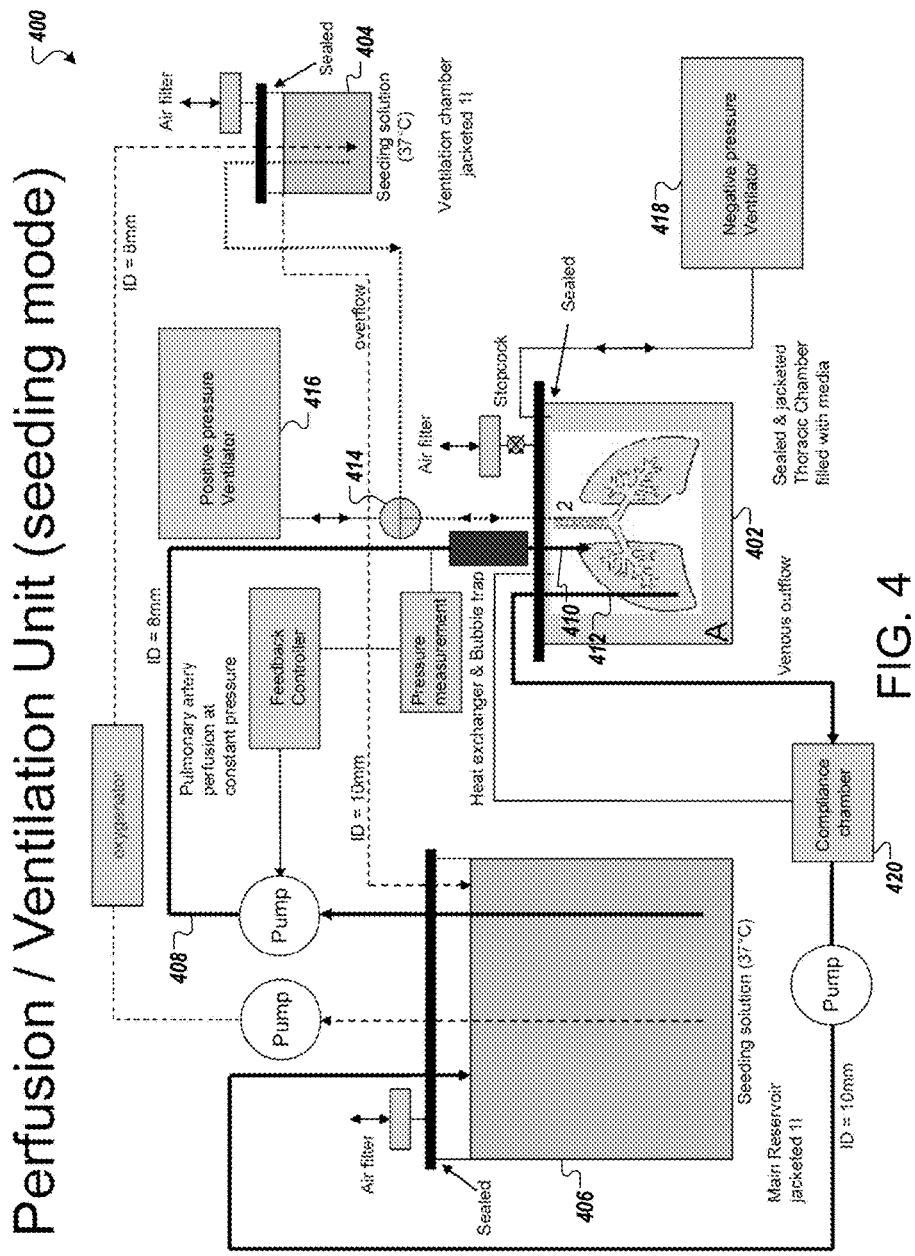
FIG. 4 is a schematic drawing of an exemplary lung bioreactor in cell seeding mode.

An exemplary airway organ bioreactor apparatus for use in cell seeding is presented in FIG. 4. Referring to FIG. 4, components of the bioreactor include lung chamber 402, sealed gravity reservoir 404, and large reservoir 406, where reservoirs 404 and 406 contain cell media for perfusion into the lung in lung chamber 402. Cell media circulates between reservoirs 404 and 406 through reservoir feeding line 408. The pulmonary artery of the lung matrix is connected to pulmonary arterial line 410 and the pulmonary vein of the lung matrix is connected to pulmonary vein line 412, each via vascular cannulas. For cell seeding, cell media is fed from reservoir 404 through the pulmonary arterial line 410 via a pump or via gravity to the pulmonary artery. Media that flows out of the lung via the third connector 412 (venous outflow) drains to afterload compliance chamber 420 via gravity and is aspirated via afterload chamber drain to reservoir 406. Afterload chamber 420 is connected to the lung chamber 402 via the lung chamber pressure line and the reservoir 406 via pulmonary venous return line 412. The lung chamber pressure line equilibrates the pressures in lung chamber 402 and afterload chamber 420. Afterload chamber 420 is also connected to the lung chamber 402 via the trachea and wet ventilation line through three-way junction 414.

The tracheal line is connected to wet ventilation line via three-way junction 414 and its controller. Three-way junction 414 is turned, using its controller, to connect the wet ventilation line to the compliance chamber 420. Compliance chamber 420 provides positive wet airway pressure (wAP) to limit net media flow through interstitial space and the trachea while limiting airway pressure to a physiologic range. The wAP is adjusted through an adjustment of the chamber 420. As a result, a portion of the cell media drains through the pulmonary venous line 412 to reservoir 406, while a smaller portion of the cell media drains via lymphatics through the lung chamber drain line to reservoir 406.

Figure 5:
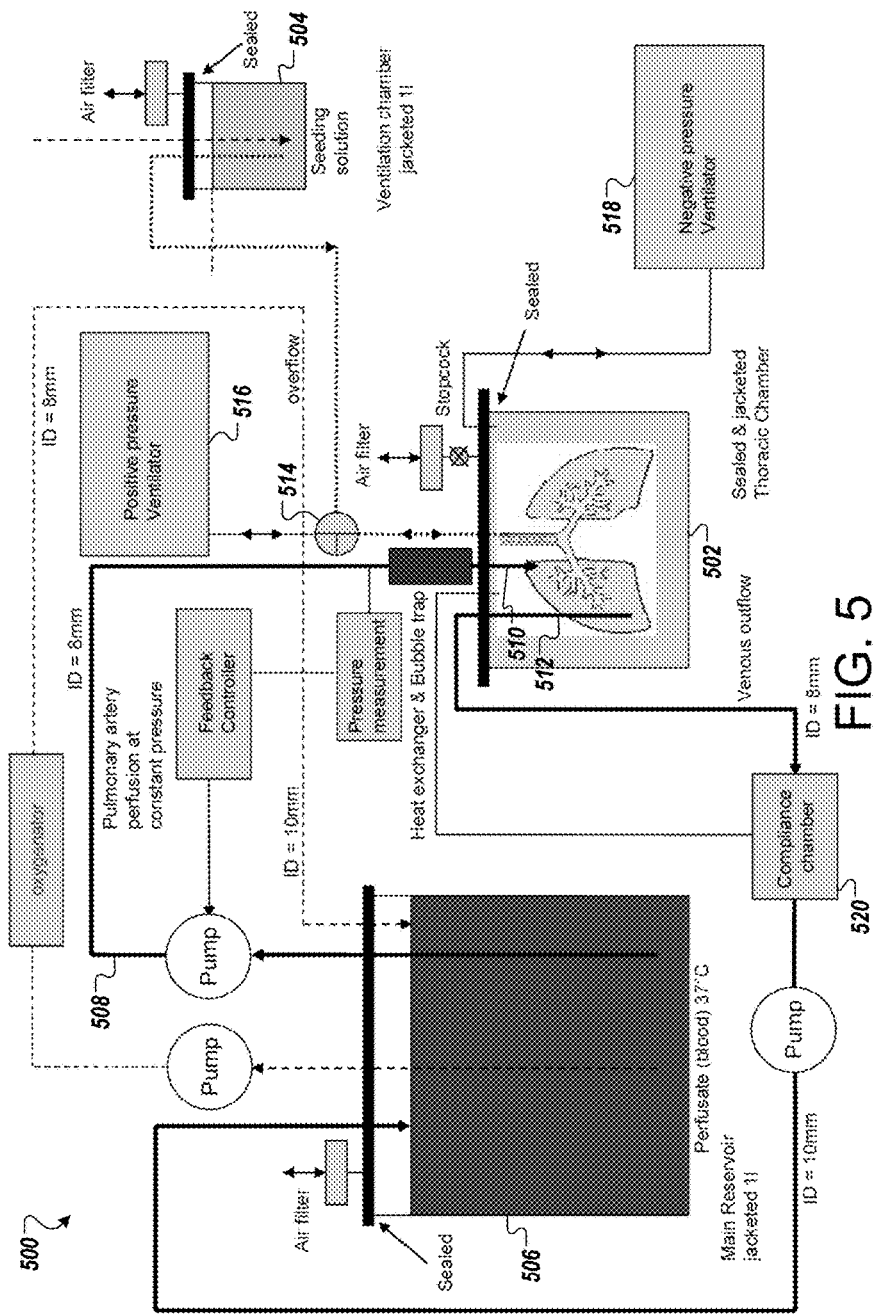
FIG. 5 is a schematic drawing of an exemplary lung bioreactor in perfusion mode.

An exemplary airway organ bioreactor apparatus for use in matrix perfusion is presented in FIG. 5. Referring to FIG. 5, components of the bioreactor include lung chamber 502, sealed gravity reservoir 504, and large reservoir 506, where reservoirs 504 and 506 contain perfusion solution (e.g., blood) for perfusion into the lung in lung chamber 502. Cell media circulates between the reservoirs 504 and 506 through reservoir feeding line 508. The pulmonary artery of the lung matrix is connected to pulmonary arterial line 510 and the pulmonary vein of the lung matrix is connected to pulmonary arterial vein 512, each via vascular cannulas. Following cell seeding, wet ventilation is needed to advance cell suspension into the peripheral airways. Wet ventilator system 518 provides wet ventilation to the lung over wet ventilation line. Then three-way junction 514 is turned, using its controller, so that the tracheal line is connected to dry ventilation line and dry ventilation system 516.

Figure 6:
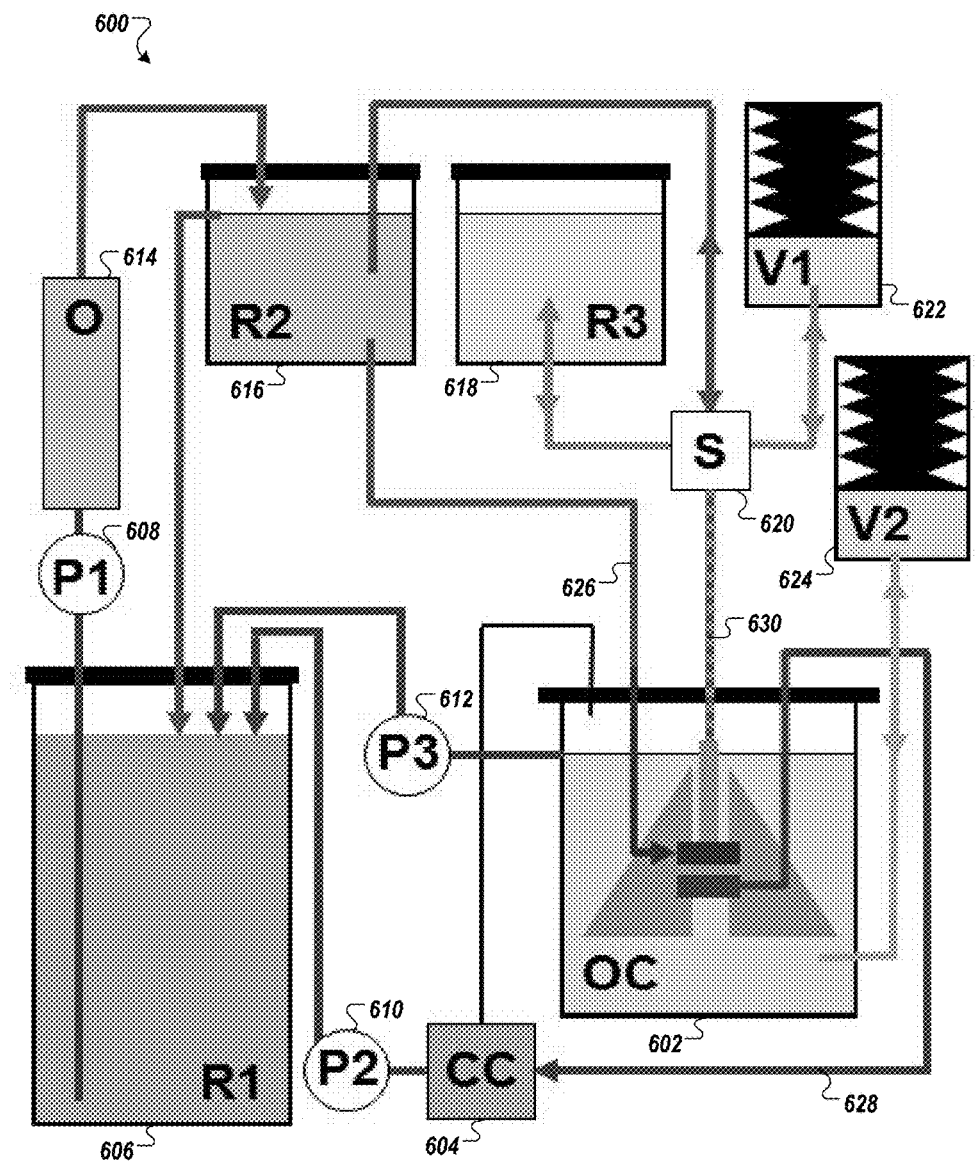
FIG. 6 is a schematic drawing of an exemplary lung bioreactor.

An exemplary airway organ bioreactor apparatus is presented in FIG. 6. Referring to FIG. 6, components of the bioreactor include lung chamber 602, sealed gravity reservoir 616, and large reservoir 606, where reservoirs 616 and 606 contain perfusion solution for perfusion into the lung in lung chamber 602. Solution circulates between the reservoirs 616 and 606 through a reservoir feeding line. The pulmonary artery of the lung matrix is connected to pulmonary arterial line 626 and the pulmonary vein of the lung matrix is connected to pulmonary arterial vein 628, each via vascular cannulas. For cell seeding, media is fed from reservoir 616 through the pulmonary arterial line 626 via a pump or via gravity to the pulmonary artery. Media that flows out of the lung via the third connector 628 (venous outflow) drains to afterload compliance chamber 604 via gravity and is aspirated via afterload chamber drain to reservoir 606. To maintain constant media level in compliance chamber 604, it can be connected to reservoir 606 via an additional line (not shown). Wet ventilator system 624 provides wet ventilation to the lung over a wet ventilation line. Three-way junction 620 is turned, using its controller, to connect wet ventilation line to compliance chamber 604.

A switch from wet to dry ventilation is made after the about 5 day period or after a monitor (not shown) determines that the lung has reached sufficient maturity. Artificial surfactant is administered via tracheal line 630. Then three-way junction 620 is turned, using its controller, so that the tracheal line 630 is connected to dry ventilation line and dry ventilation system 622. The lung is ventilated to slowly fill its airspace with gas rather than fluid.

The invention will be further described in the following examples, which do not limit the scope of the invention described in the claims.

EXAMPLE

Lung Regeneration Based on Perfusion Decellularized Matrix Scaffolds

Lungs were isolated from heparinized adult SD rats (n=20) and decellularized using detergent perfusion. Resulting extracellular matrix (ECM) scaffolds were analyzed using histology, electron microscopy and mechanical testing. Scaffolds were mounted in a bioreactor and seeded with human umbilical cord endothelial cells (HUVEC, n=4), HUVECs and human alveolar basal epithelial cells (H-A549, n=4), and HUVECs and rat fetal lung cells (H-FLC, n=2). Culture was maintained up to seven days. Lung function was analyzed in an isolated lung apparatus using blood perfusion and ventilation, normal lungs served as controls (n=4).

Perfusion decellularization of cadaveric lungs yielded acellular lung ECM scaffolds with intact airway and vascular architecture. Lung scaffolds could be repopulated with endothelial and epithelial cells and maintained in a bioreactor. Gas exchange ($PaO_2/FiO_2$ ratio) was lower in H-A549 constructs (103.6 mmHg), and equal in H-FLC constructs (455.1 mmHg) compared to normal lung (465.8 mmHg). Compliance was reduced in decellularized lungs (0.27 ml/cmH$_2$O/s), but equal in H-FLC constructs (0.67 ml/cmH$_2$O/s) and normal lung (0.69 ml/cmH$_2$O/s).

Perfusion decellularization of cadaveric lungs yields intact whole lung ECM scaffolds that can be seeded with epithelial and endothelial cells to form bioartificial lungs with ventilation, perfusion and gas exchange comparable to normal lungs.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An airway organ bioreactor apparatus, comprising:
an organ chamber configured to hold an organ matrix scaffold onto which a cell media is perfused to grow an organ;
a flow perfusion system configured for perfusion seeding, the flow perfusion system comprising:
   a reservoir system configured to contain a first cell media having at least one of differentiated or regenerative cells suspended in the cell media and a second cell media,
   a pulmonary arterial line fluidly coupling a first reservoir of the reservoir system to the organ chamber, and
   a pumping system coupled to the reservoir system and configured to supply the first cell media from the first reservoir of the reservoir system to the organ chamber over the pulmonary arterial line to provide a fluid level in the organ chamber, the pumping system configured to drain waste media from the organ chamber to a second reservoir of the reservoir system over at least one drain line;
a wet ventilator system configured to supply a wet ventilation to an organ airspace of the organ;
a dry ventilator system configured to supply a dry ventilation to the organ airspace of the organ;
a tracheal line selectively fluidly coupling the organ chamber with the reservoir system, the dry ventilator system, and the wet ventilation system; and
a controller configured to control delivery of wet ventilation and delivery of dry ventilation, the controller configured to: cause seeding of the organ airspace with the second cell media via the tracheal line, cause an increase in a positive wet airway pressure provided via the tracheal line after seeding of the organ airspace, cause initiation of wet ventilation after a period of perfusion seeding of a pulmonary vasculature with the first cell media via the flow perfusion system, and switch from wet ventilation to dry ventilation after a period of wet ventilation so as to drain wet fluid from the organ airspace so as to fill the organ airspace with gas.

2. The apparatus of claim 1, further comprising:
a first three-way junction configured for selectively fluidly coupling the tracheal line with a first branch and a second branch, the three-way junction including a switch configured to toggle between the first branch and the second branch;
wherein:
the wet ventilator system is configured to supply a wet ventilation to the organ via the first branch;
the dry ventilator system is configured to supply a dry ventilation to the organ via the second branch; and
the controller is configured to control the switch of the first three-way junction, thereby controlling delivery of wet ventilation or delivery of dry ventilation.

3. The apparatus of claim 2, wherein the at least one drain line comprises a first branch, a second branch, and a third branch; and
a second three-way junction at which the first branch of the at least one drain line and the second branch of the at least one drain line are connected with the third branch of the at least one drain line.

4. The apparatus of claim 2, wherein the wet ventilator system comprises:
a wet ventilator connected to the organ chamber via a wet ventilation line; and
a compliance chamber connected to the organ chamber via the first three-way junction.

5. The apparatus of claim 4, wherein a wet positive and expiratory pressure (wPEEP) is provided to the organ chamber via an elevation of the compliance chamber.

6. The apparatus of claim 4, further comprising
an afterload chamber connected to:
the organ chamber via the second branch of the at least one drain line, and
the reservoir system via a return line.

7. The apparatus of claim 6, wherein the reservoir system comprises:
the first reservoir connected to the organ chamber via the pulmonary arterial line; and
the second reservoir connected to:
the organ chamber via an organ chamber drain, and
the afterload chamber via the return line,
wherein the first reservoir and second reservoir circulate media over a reservoir feed line and a reservoir drain.

8. The apparatus of claim 3, wherein the dry ventilator system comprises:
a dry ventilation chamber including a nebulizer, connected to the organ via the second branch of the three-way junction; and
a first dry ventilator configured to provide a dry positive and expiratory pressure (dPEEP) to the organ chamber and connected to the dry ventilation chamber via a dPEEP line.

9. The apparatus of claim 8, wherein the dry ventilator system further comprises:
a second dry ventilator connected to the organ chamber via a dry ventilator line.

10. The apparatus of claim 8, further comprising
a gas tank configured to supply gaseous media to the organ chamber, the dry ventilation chamber, and the reservoir system.

11. The apparatus of claim 1, wherein the controller is operated by a computer.

12. The apparatus of claim 1, wherein the pumping system of the flow perfusion system is configured to pump cell media from the organ chamber via the at least one drain line to maintain the fluid level in the organ chamber at a constant level.

* * * * *

UNITED STATES PATENT AND TRADEMARK OFFICE
CERTIFICATE OF CORRECTION

PATENT NO. : 10,059,913 B2
APPLICATION NO. : 14/685158
DATED : August 28, 2018
INVENTOR(S) : Harald C. Ott Page 1 of 1

It is certified that error appears in the above-identified patent and that said Letters Patent is hereby corrected as shown below:

On the Title Page

Item (54) and the Specification, Column 1, Line 1, delete "BIOARTIFICAL" and insert
-- BIOARTIFICIAL --

Signed and Sealed this
Fifth Day of March, 2019

Andrei Iancu
*Director of the United States Patent and Trademark Office*